United States Patent [19]

Barton

[11] Patent Number: 5,046,580

[45] Date of Patent: Sep. 10, 1991

[54] EAR PLUG ASSEMBLY FOR HEARING AID

[76] Inventor: James I. Barton, 31315 E. Nine Dr., Laguna Niguel, Calif. 92677

[21] Appl. No.: 569,392

[22] Filed: Aug. 17, 1990

[51] Int. Cl.$^5$ .................................... A61B 7/02

[52] U.S. Cl. .................................... 181/135; 381/68.6; 381/68.7; 128/866

[58] Field of Search .................................... 181/130, 135; 128/864-868; 381/68.6, 68.7

[56] References Cited

U.S. PATENT DOCUMENTS 1,279,396 9/1918 Michelson .................... 128/868
3,732.382 5/1973 DeWitt .................... 181/130 X
4,539,440 9/1985 Sciarra .................... 381/68.6 X

*Primary Examiner*—Brian W. Brown
*Attorney, Agent, or Firm*—Charles D. Brown

[57] ABSTRACT

An ear plug assembly (28) for behind the ear hearing aids. The ear plug assembly (28) comprises a hollow substantially conical shell (32) having two annular ridges (42, 44) in its smaller open end (34). A hollow tube (26) connects the electronics package (20) to the smaller end (34) of the shell (32) and conveys the sound into the ear canal. One end of the tube (26) has a fitting or endpiece (50) in it with a flange (52) that is seated between the ridges thus securing the tube (26) in the shell. A slidable nut (38) and a spring (40) are mounted on the tube (26) such that the nut can be slid toward the endpiece (50) thus compressing the spring (40) and providing rigidity. The compressed spring (40) transmits a force applied to the nut (38) to act upon the endpiece (50) and the ridge (44) of the shell (32). This force tends to stretch the shell (32), reducing its diameter so that easier and deeper insertion into the ear canal can be achieved. When the force is removed from the nut (38), the shell (32) tends to return to its noraml size i.e. its larger diameter, and hence achieves a snug and comfortable fit with the interior of the ear canal of the wearer.

6 Claims, 1 Drawing Sheet

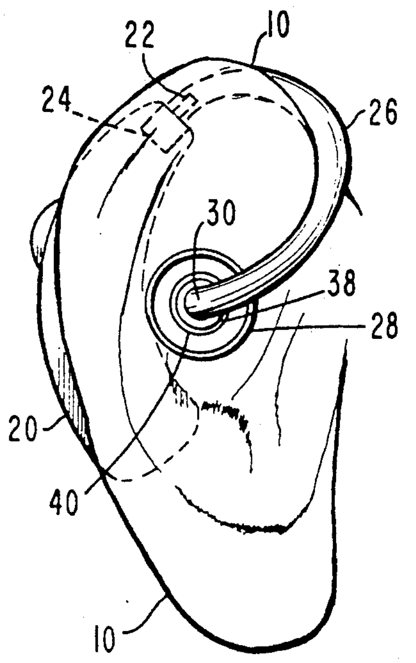
Fig. 1.
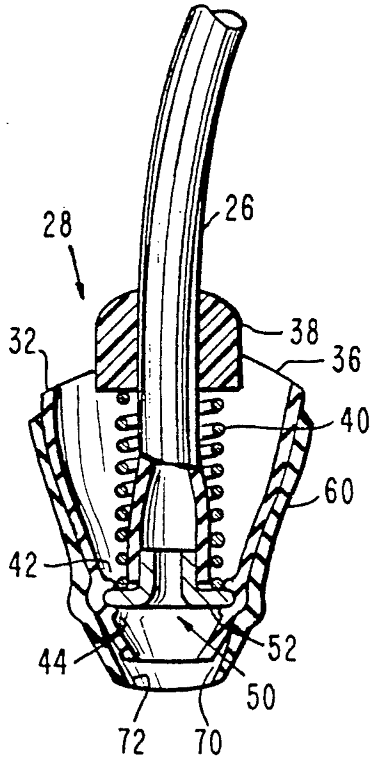
Fig. 3.
Fig. 2.
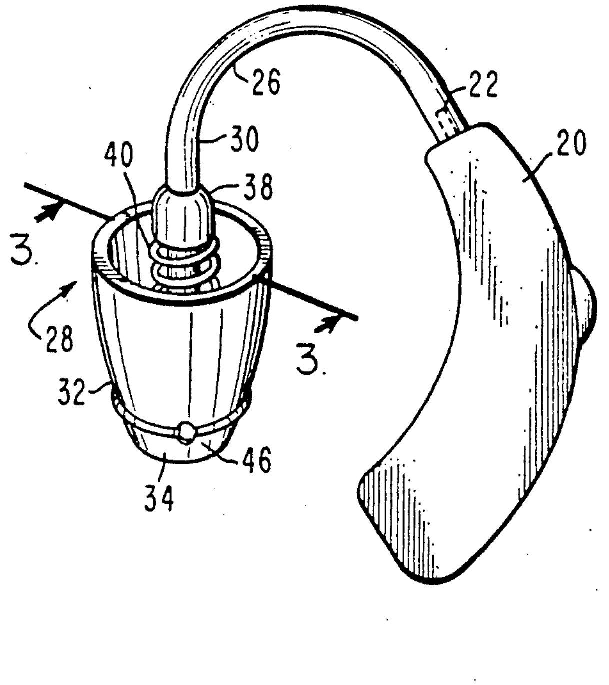
Fig. 4.
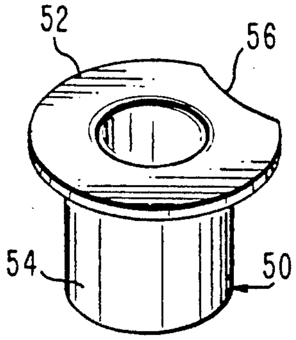

EAR PLUG ASSEMBLY FOR HEARING AID

BACKGROUND

1. Field of the Invention

This invention relates to hearing aids and in particular to improvements to the ear plug of the type of hearing aid known as a behind-the-ear (BTE) hearing aid.

2. Related Art

Various kinds of hearing aids are readily available. One of the most desirable is the "canal" hearing aid which uses miniaturized electronics and is encased in a rigid container which is inserted into the wearer's ear canal. Only a small portion of the canal aid extends outside the ear canal, including the microphone and volume adjustment devices. The battery, electronics and speaker are housed in the casing which preferably has been conformed to the shape of the ear canal for best fit. At this point it should be noted that in the hearing aid industry the speaker is called the "receiver" and thus throughout the remainder of this description the word receiver will be used to identify the speaker.

A second recognized type of hearing aid is the in-the-ear (ITE) hearing aid. This type of hearing aid is much larger than the canal aid and in addition to having a portion (including the receiver) which extends into the ear canal, also has a portion which is outside the ear canal and occupies the bowl of the ear immediately adjacent the ear canal.

In a third type of hearing aid the electronics and receiver are located remote from the ear canal and may be packaged to fit (for example) behind-the-ear (BTE). The sound is conveyed from the receiver to the ear canal by a flexible tube such as a plastic tube. One end of the tube fits over the receiver outlet of the behind-the-ear electronics package and the other end extends through an ear plug (which is hollow but otherwise shaped much like a canal hearing aid) to the interior of the ear canal. The volume control and battery are located with the BTE electronics package. In order to connect the receiver with the ear plug, the plastic tube must make a number of turns, the most severe of which is that immediately upon entering the ear plug. That turn is so sharp that the tubing frequently collapses thus reducing and distorting the internal cross section of the tubing and causing a reduction in the volume and quality of sound reaching the interior of the ear canal.

SUMMARY OF THE INVENTION

The invention comprises a new form of ear plug assembly designed specifically to overcome the problems described above (and others) for behind-the-ear (BTE) hearing aids.

Specifically, the invention includes a hollow substantially conical shell made of a relatively soft and flexible elastomer or silicon rubber or other similar material which has been approved for such use (i.e. wearing in the ear canal) by the Food and Drug Administration. The shell can be used in a variety of sizes such that when a given size is inserted into the ear canal of a user, the shell will deform and conform to the shape of the ear canal ensuring a proper and comfortable fit. This feature eliminates the need to make an impression of the ear canal as must be done when fitting a person with a hard plastic hearing aid (either ITE or canal aid). The ear plug assembly is connected to the receiver of the behind-the-ear electronics package by a plastic tube. The ear plug assembly includes a hollow substantially conical shell member having a large open end and a smaller open end with two annular ridges located on the interior of the smaller open end defining a valley between them. The ear plug assembly also includes a length of plastic tubing and a flanged metal endpiece which is inserted into one end of the tube, as well as a loosely coiled wire spring and an annular plastic "nut".

The ear plug assembly may be assembled as follows. The flanged metal endpiece is inserted into one end of the plastic tube. The other end of the tube is inserted through the smaller end of the shell member and pushed out the larger end of the shell. The flange of the metal endpiece is worked until the flange is properly seated between two annular ridges located on the interior of the small end of the shell. The spring is then placed over the free end of the tube and pushed toward the metal flange until it contacts the first of the annular ridges on the interior of the small end of the shell. The annular plastic "nut" is then also slid over the free end of the tube and moved into contact with the spring.

To improve the tonal qualities of the sound, and to prevent the sensation of "listening at the bottom of a barrel" (as with some older model telephones) a vent may be provided connecting the interior volume of the ear canal to the interior volume of the ear plug (but outside the tube) and thereby to the outside environment (i.e. outside of the ear). The vent consists of one or more holes in the body of the shell member to allow communication of outside air past the shell to the interior of the ear canal. A harness such as described in my U.S. Pat. No. 4,869,339 Harness For Suppression of Hearing Aid Feedback, issued Sept. 26, 1989, may be mounted over the ear plug assembly provided care is taken not to cover the vent with the harness. The content of that U.S. patent is hereby incorporated herein by this reference.

BRIEF DESCRIPTION OF THE DRAWINGS

FIG. 1 shows a behind-the-ear electronics package and plastic connecting tube with the ear plug assembly of the present invention.

FIG. 2 is a perspective view showing the new ear plug assembly in greater detail.

FIG. 3 is a cross section illustrating the ear plug assembly with a harness in place over the new ear plug.

FIG. 4 is a perspective showing the flanged endpiece in greater detail.

DETAILED DESCRIPTION OF THE INVENTION

FIG. 1 shows the typical configuration for a behind-the-ear (BTE) hearing aid. Such hearing aids are sized and shaped to fit comfortably behind the ear 10 and against the head of the wearer. The BTE electronics package 20 includes elements typical of nearly all hearing aids such as a housing, a microphone, battery, amplifier circuits, filter circuits, volume adjustment controls, and a receiver. Only the receiver 22 and its wire leads 24 are shown in FIG. 1. The operation of such a device is well known and will not be described herein except to note that the sound output by receiver 22 is conveyed by tube 26 through an ear plug 28 to the interior of the user's ear canal. As seen in FIG. 1, the tube 26 must make a number of bends. The sharpest bend 30 occurs at the entrance to the ear plug 28. Such a sharp bend frequently causes collapse and distortion of the interior volume of the plastic tube 26 at the bend 30, resulting in reduction in volume and distortion in the tonal quality of sound reaching the eardrum.

The new ear plug assembly 28 shown in greater detail in FIG. 2 and in cross section in FIG. 3, alleviates the problem of collapse of the plastic tube 26 by using a tube which has been manufactured with a preformed bend. The ear plug assembly 28 includes a hollow generally conical shell 32 made of a soft plastic or silicon elastomer. The shell may be a standard item such as manufactured by Chavers Gasket Corp. in Laguna Hills, Calif. and identified by various part numbers depending upon size, or may be custom made. The wall of the shell is preferably between approximately 0.05 and 0.01 inch thick. The shell 32 is preferably formed with two annular ridges 42 and 44 on the interior of the small end 34 of the shell, as more fully described below. Because the shell is easily deformed it will conform to the shape of a wearer's ear canal, without the need to make an impression of the canal, thus insuring a good and comfortable fit and enabling a dispenser of hearing aids to test and fit a customer and provide the hearing aid to the customer in about one hour. The smaller end 34 is intended to be inserted deep into the ear canal so that the larger end 36 fits slightly inside the outer opening of the ear canal.

The deep insertion of the shell 32 into the ear canal is accomplished as follows. The ear plug assembly 28 is loosely inserted into the ear canal. The wearer then uses the forefinger to exert force upon the larger end 36 of the shell 32. This will insert the shell 32 a little more deeply into the ear canal. Full insertion of the shell 32 to its intended depth cannot be accomplished by pushing on the large end of the shell 32 because the shell is very flexible and would tend to collapse. To achieve full insertion depth, the wearer grasps the plastic "nut" 38 between the thumb and forefinger and pushes the "nut" axially along the tube 26 toward the spring 40. This tends to compress the spring 40 and also transfers the force to the other end of the spring 40 to act upon the first annular ridge 42. The application of this force tends to stretch the shell member 32 and consequently reduce its exterior diameter (in the same way that a stretched rubber band becomes thinner) thus permitting easier and deeper insertion of the small end 34 of shell 32 into the ear canal. When the wearer stops exerting force upon the "nut" 38 the shell member 32 tends to return to its natural length and natural (larger) diameter thus forming a more snug fit with the interior wall of the ear canal. This deep insertion and snug fit eliminate virtually all feedback that otherwise would cause unpleasant squealing in the wearer's ear. In addition, a sufficiently deep insertion may overcome the unpleasant "hollow" sound and eliminate the need for a vent 46, depending on the wearer's particular hearing characteristics and hearing aid power output.

Tube 26 extends from the receiver 22 (see FIG. 1) to the small end 34 of shell 32 to convey sound emitted by the receiver to the interior of the ear canal. Because the passageway of the ear canal is generally perpendicular to the side of a person's head, that portion of the plastic tube 26 which extends through the ear plug 28 and into the ear canal is also substantially perpendicular to that portion of the tube 26 which lies against the person's head at the point where the tube attaches to the electronics package 20. Thus bend 30 is approximately a ninety degree bend. Such a bend can easily cause a straight plastic tube 26 to at least partially collapse at the bend 30 thereby reducing its interior cross sectional area and reducing the volume of sound reaching the wearer's eardrum. To prevent collapse of the tube 26 at bend 30 tube 26 is either manufactured with bend 30 formed into the tube at the time of manufacture, or the bend is formed just prior to assembly of the ear plug assembly 28. Thus the passageway inside tube 26 is not constricted nor distorted and the volume of sound transiting bend 30 to the wearer's eardrum is not reduced.

Preferably the spring 40 is a metal spring and is chosen such that the inside diameter of its coils will cause a close but not snug fit with the outside diameter of the tube 26. The spring 40 does not have to be tightly coiled, i.e., the coils do not have to contact one another and preferably are somewhat spaced apart. This permits the spring 40 to be compressed by sliding nut 38 toward the endpiece 50. The compressed spring provides the rigidity required to facilitate deeper insertion of earplug 28. Without spring 40, application of force to nut 38 would likely cause collapse of the tube 26 before sufficient force could be applied to cause the needed deep insertion of shell member 32. Initially, insertion is accomplished by pressing on the open large end 36 of shell 32. But the earplug described herein is intended to be inserted so deep into the ear canal that the large end 36 is not easily accessed; and further, the shell 32 is too flexible to transmit sufficient force to accomplish deep insertion. Thus, by grasping the slidable nut 38 and pushing inward so as to compress the spring 40, the spring becomes rigid and can assist in placing the ear plug assembly 28 deeper into the ear canal.

If the ear plug assembly 28 including the tube 26 was connected to the electronics package 20 and then inserted into the ear canal, the ear plug assembly and the tube would seal off the ear canal and the wearer would have the sensation of listening at the bottom of a barrel. The sound would have a very unnatural quality. To avoid this, a vent 46 is provided between the interior of the ear canal and the air volume outside the ear canal. This is implemented by making one or more holes (vents) 46 in the body of the shell member 28 as shown in FIG. 2. The vent 46 located in a radially juxtaposed position with respect to a notch 56 which is made in the flange 52 of the endpiece 50. By virtue of the vent, air can freely travel from one side of the flange to the other thus eliminating the undesirable "hollow" sound effect. However, as explained above, if the ear plug assembly 28 is inserted sufficiently deep into the ear canal, the need for the vent may be obviated.

In order to securely affix tube 26 to endpiece 50, a suitable adhesive such as sold under the trademarks Super Glue or Crazy Glue may be used to glue the outer cylindrical surface 54 of endpiece 50 to the interior surface of tube 26. However, it is important not to glue endpiece 50 to the interior surface of shell 32 nor to the annular ridges 42 or 44. To do so would prevent easy disassembly of the ear plug assembly such as for cleaning and sterilization.

In order to prevent the endpiece 50 and the tube 26 from passing out through the small end 34 of shell 32 during the insertion of the ear plug assembly into the ear canal, two annular ridges 42 and 44 are formed on the interior surface of shell 32. For added safety, the ridge 44 nearest the opening in the small end 34 can be made higher than the other ridge. The two ridges should be spaced apart only far enough to permit the flange 52 of endpiece 50 to seat itself between them.

The improved ear plug assembly as thus far described can be used and satisfactory hearing, substantially improved over prior art ear plugs, can be obtained. However, further benefits can be obtained if a harness 60, as described in my U.S. Pat. No. 4,869,339, is mounted on the ear plug assembly 28 as shown in FIG. 3 in cross section. The harness should be of a size such that when installed on the ear plug assembly there is a small gap 70, on the order of 0.010 to 0.030 inch between the outer surface of the small end 34 of shell 32 and the interior surface 72 of the harness 60. This gap 70 allows the shell 32 to "float" within the harness, and because the harness is much more flexible than shell 32, it will readily deform and follow the curved shape of the interior of the wearer's ear canal thereby providing a "guide" for shell 32 easing its insertion into the ear canal and ensuring a proper and comfortable fit. Use of the harness 60 provides the same benefits as described in U.S. Pat. No. 4,869,339. Thus, the ear plug does not work loose in the ear canal during normal exercise of jaw muscles such as occurs when talking or chewing.

There has thus been provided an ear plug assembly with the unique feature that when in its natural state has no rigid parts that could damage the ear upon insertion into the ear canal. Yet, when rigidity is required to facilitate deep insertion, the wearer applies force to the nut, compressing the spring which provides sufficient rigidity to transmit the force to the small end of the ear plug assembly thereby effecting easy and deep insertion. When insertion is completed and force is removed from the nut, the spring expands, loses its rigidity and thus again no rigid parts are present that could accidentally damage the ear. The ear plug assembly thus provides for rigidity only when rigidity is needed, during the insertion process.

While the invention has been described with reference to its preferred embodiment, it is understood that one of ordinary skill in the art having the benefits of the teachings disclosed herein, could make various changes, modifications and additions to the invention without departing from the spirit and scope of the invention.

As described herein the spring 40 serves to provide rigidity on demand. Other devices may be used which are also longitudinally flexible yet, when required, can be made sufficiently rigid to transmit force to the small end of the shell thus stretching it for easy insertion. Thus, when used herein, the term spring is intended to mean the spring and any other functionally equivalent alternate. Similarly, the ridges and endpiece serve to secure the end of the tube to the interior surface of the small end of the tube. Other equivalent alternatives may be provided without the exercise of the inventive faculties and such equivalents are intended to be included within the scope of the invention.

Thus, the scope of the invention is intended to be limited only by the appended claims. As can plainly be seen upon a cursory reading, the claims are not limited to an ear plug used in conjunction with a behind-the-ear hearing aid. Indeed the claims are not limited to any particular kind of hearing aid and any future or present kind of hearing aid, including in-the-ear and canal aids, may be readily adapted by a person of ordinary skill in the art for use in connection with the claimed invention.

What is claimed is:

1. An improved ear plug assembly for use with a hearing aid comprising an electronic package which includes a receiver, an ear plug assembly and a tube having a first end which connects to the receiver and a second end which connects to the ear plug assembly, said improved ear plug assembly comprising:

a flexible hollow generally conical shell member having an interior surface and an exterior surface and a large open end and a small open end;

means for securing said second end of said tube to the interior surface of the small open end of said shell member;

a spring, having an inner diameter greater than an outside diameter of said tube, mounted upon and circumscribing the tube and having a first end proximate said means for securing; and slidable annular nut means mounted upon said tube for contacting a second end of said spring.

2. The ear plug assembly of claim 1 wherein said means for securing comprises:

a first annular ridge located on the interior surface of the small end of said shell;

a second annular ridge located on the interior surface of said small end of said shell and slightly axially spaced from said first annular ridge to define a groove therebetween;

an endpiece having a cylindrical portion for mating with said tube and a radially extending flange portion for seating in said groove.

3. The ear plug assembly of claim 2 wherein said endpiece mating with said tube is secured by an adhesive.

4. The ear plug assembly of claim 1 further comprising a harness, said harness having an interior surface and an exterior surface, the interior surface having a diameter larger than an outside diameter of the smaller end of said shell, thereby defining a gap between said harness and the small end of said shell.

5. The ear plug assembly of claim 4 wherein said gap is between approximately 0.010 and 0.030 inch.

6. The ear plug assembly of claim 2 further comprising vent means for allowing passage of air from inside an ear canal of a wearer to outside said ear canal, said vent means comprising:

a notch in the flange of said endpiece; and a hole in the shell, said hole being radially aligned and juxtaposed with said notch.

* * * * *